United States Patent [19]

Miwa et al.

[11] Patent Number: 5,020,842
[45] Date of Patent: Jun. 4, 1991

[54] INSTRUMENT FOR INOCULATING BULB SCALES

[75] Inventors: Yoshiyuki Miwa; Hiroshi Kodama; Skinya Murasugi, all of Tokyo; Sadao Shikae, Kagoshima; Masaya Nakagawa; Tsutomu Kabumoto, both of Tokyo, all of Japan

[73] Assignees: Waseda University; Mitsubishi Jukogyo Kabushiki Kaisha, both of Tokyo, Japan

[21] Appl. No.: 398,421

[22] Filed: Aug. 25, 1989

[30] Foreign Application Priority Data

Sep. 2, 1988 [JP] Japan ................................ 63-218510

[51] Int. Cl.⁵ ........................ B25J 15/06; B65G 47/91
[52] U.S. Cl. .................................... 294/2; 47/1.01; 294/64.1; 294/86.4; 901/31; 901/40
[58] Field of Search .................. 294/1.1, 2, 64.1, 86.4, 294/99.1, 103.1, 104, 106; 47/1.01, 57.6, 58, DIG. 9; 414/606, 618, 626, 729–732, 736, 737, 739, 752, 753; 901/30–32, 36, 38–40, 50

[56] References Cited

U.S. PATENT DOCUMENTS

| | | |
|---|---|---|
| 3,651,957 | 3/1972 | Ball et al. ............................ 294/2 X |
| 4,473,247 | 9/1984 | Itemadani et al. ...................... 294/2 |
| 4,515,508 | 5/1985 | Takamatsu ...................... 294/64.1 X |
| 4,582,353 | 4/1986 | Alvernhe . |
| 4,627,785 | 12/1986 | Monforte ............................ 294/2 X |
| 4,787,805 | 11/1988 | Kosikowski ........................ 294/2 X |
| 4,909,376 | 3/1990 | Herndon et al. ................. 901/40 X |

FOREIGN PATENT DOCUMENTS

| | | |
|---|---|---|
| 0198501 | 10/1986 | European Pat. Off. . |
| 0232628 | 8/1987 | European Pat. Off. . |
| 2847473 | 12/1979 | Fed. Rep. of Germany . |
| 2550985 | 3/1985 | France . |
| 246721 | 6/1987 | German Democratic Rep. ... 901/40 |
| 925836 | 5/1982 | U.S.S.R. ................................ 294/2 |
| 1400876 | 6/1988 | U.S.S.R. ................................ 294/2 |

*Primary Examiner*—Johnny D. Cherry
*Attorney, Agent, or Firm*—Fleit, Jacobson, Cohn, Price, Holman & Stern

[57] ABSTRACT

Disclosed herein is an instrument for inoculating bulb scales which comprises an instrument line, a scale sucking finger having a suction tube, and a scale gripping finger, with one end thereof rotatably joined to the instrument proper and with an intermediate part thereof connected to the instrument proper with a spring made of shape memory alloy.

2 Claims, 1 Drawing Sheet

FIG. 1
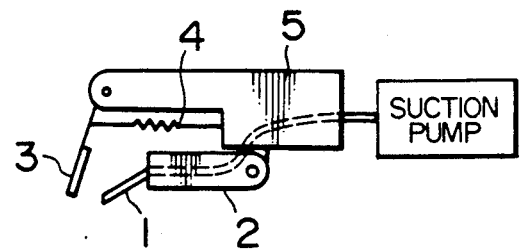
FIG. 2(A)   FIG. 2(B)   FIG. 2(C)
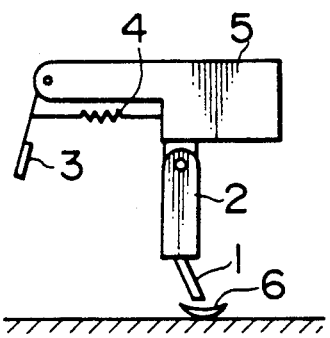 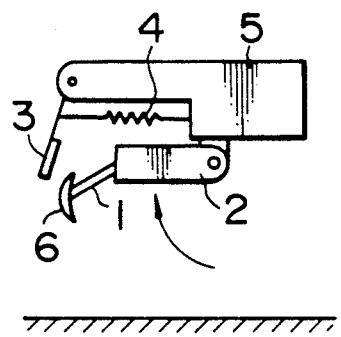 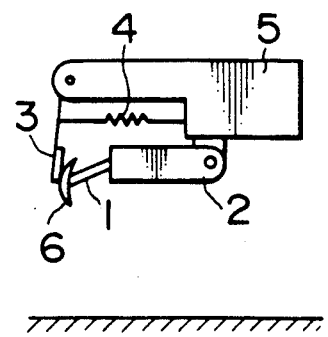
FIG. 3
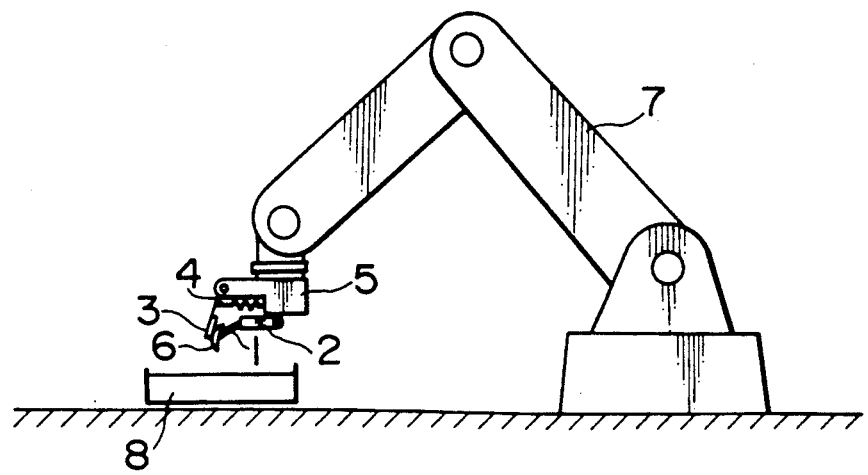

INSTRUMENT FOR INOCULATING BULB SCALES

FIELD OF THE INVENTION AND RELATED

The present invention relates to an instrument for inoculating bulb scales.

The procedure for tissue culture of bulbous plants such as lily, black lily, and Fritillaria verticillata involves the steps of dividing a bulb into scales and placing them on an agar medium under aseptic conditions. These steps used to resort to handwork which is carried out using a forceps in a clean bench. Therefore, not only does the conventional procedure need many instruments and materials and much handwork but it also suffers from a disadvantage that scales are contaminated with germs carried by the human body. One possible way to eliminate this disadvantage is to mechanize the procedure by using, for example, a robot hand. Mechanization, however, has been difficult to realize because the small scales have to be gripped securely without any damage to their tissue.

OBJECT AND SUMMARY OF THE INVENTION

It is an object of the present invention to provide an instrument for inoculating bulb scales which is able to perform the procedure more conveniently and efficiently than handwork under improved aseptic conditions.

The gist of the present invention resides in an instrument for inoculating bulb scales which comprises an instrument body, a scale sucking finger having a suction means, and a scale gripping finger, with one end thereof rotatably joined to the instrument body and with an intermediate part thereof connected to the instrument body with a spring made of shape memory alloy.

An embodiment of the present invention is shown in FIG. 1. There is shown a suction tube 1 connected to a suction pump (not shown). There is shown a scale sucking finger 2 which is movably joined to the instrument body 5. (The suction tube 1 passes through the scale sucking finger 2.) There is shown a scale gripping finger 3, which is movably attached to the instrument body 5 at its one end and is also connected to the instrument body 5 at its intermediate position by means of a spring 4 made of shape memory alloy.

Having the structure as mentioned above, the instrument of the present invention has the following features. When the spring 4 of shape memory alloy undergoes temperature change, it expands or contracts to change the position of the scale gripping finger 3. This movement closes or opens the clearance between the scale sucking finger 2 and the scale gripping finger 3. With the clearance closed, the two fingers hold a scale, and with the clearance opened and the suction removed, the two fingers let the scale fall.

The instrument of the present invention is operated in the following manner. With the scale sucking finger 2 directed downward, suction is applied to the suction tube 1 by turning on the suction pump, in order that the suction tube 1 sucks up a scale placed on a flat surface. (Suction permits a scale, no matter how small and soft it might be, to be securely held by the tip of the suction tube 1.) The instrument carrying a scale is brought to a position above the culture medium into which the scale is inoculated. The spring 4 of shape memory alloy is caused to change in temperature by applying an electric current or by other means, so that it contracts slowly. Simultaneously, the scale sucking finger 2 is raised so that the scale is held between the tip of the scale gripping finger 3 and the tip of the scale sucking tube 1. The instrument holds the scale with sufficient force for inoculation and without damaging it. Then the instrument is moved downward to press the scale against the culture medium for inoculation. The spring 4 of shape memory alloy is caused to change in temperature so that it expands and hence the scale gripping finger 3 opens. Suction is removed from the suction tube 1. Thus the scale parts from the instrument easily. By repeating the above-mentioned procedure, it is possible to inoculate scales securely with the sensitivity at least comparable to the human hand without any damage to scales. The detail of the inoculating operation will be explained with reference to the example which follows.

The instrument of the present invention may be attached to a general-purpose positioning apparatus such as a 6-axis robot arm, so that it can be moved to desired positions for picking up and placing a scale. The above-mentioned inoculating procedure, which is carried out in a clean bench using the instrument of the invention which has been sterilized, will automate the steps for inoculation, increase the efficiency of inoculation, and improve the aseptic conditions for inoculation.

The present invention produces the effects of carrying out the steps of scale inoculation with certainty and gentleness comparable to or even better than handwork, mechanizing the steps of scale inoculation, increasing the efficiency of scale inoculation, saving the labor for scale inoculation, improving the aseptic conditions for scale inoculation, and performing the procedure of scale inoculation uniformly regardless of operators.

BRIEF DESCRIPTION OF THE DRAWINGS

FIG. 1 is a schematic representation of an embodiment of the instrument for inoculating bulb scales pertaining to the present invention. FIGS. 2(A), 2(B), and 2(C) are schematics explaining the steps of inoculating bulb scales with the instrument of the present invention. FIG. 3 is a schematic representation showing the instrument of the invention which is attached to a robot arm.

DETAILED DESCRIPTION OF THE PREFERRED EMBODIMENTS

An example of the present invention will be described with reference to FIGS. 1 to 3. The instrument for inoculating bulb scales is made up of a suction tube 1, a scale sucking finger 2, a scale gripping finger 3, a spring 4 made of shape memory alloy, and an instrument body 5. The suction tube 1 is connected to a suction pump (not shown) and passes through the scale sucking finger 2. The scale sucking finger 2 is rotatably joined to the instrument body 5 so that it can be turned 90° downward. The scale gripping finger 3 is also rotatably joined to the instrument body 5. The spring 4 made of shape memory alloy is attached to the scale gripping finger 3 and the instrument body 5, so that it changes the clearance between the scale sucking finger 2 and the scale gripping finger 3 (or opens or closes the two fingers) as it expands or contracts. The spring 4 of shape memory alloy has the memory of its contracted state in this case so that it contracts when it is heated to a prescribed temperature by the application of an electric current. As the spring 4 contracts, the scale gripping finger 3 slowly moves toward the tip of the suction tube 1.

FIGS. 2(A), 2(B), and 2(C) show the steps of the instrument sucking up a scale and gripping it. With the scale sucking finger 2 directed downward, suction is applied to the suction tube 1 by a suction pump connected to it, so that the tip of the suction tube 1 picks up a scale 6, as shown in FIG. 2(A).

With suction applied by the suction pump, the scale sucking finger 2 is moved upward as shown in FIG. 2(B). Finally, an electric current is applied across the spring 4 of shape memory alloy, so that the spring 4 contracts, causing the scale gripping finger 3 to press gently against the scale 6 which has been sucked up by the suction tube 1, as shown in FIG. 2(C).

The scale gripping finger 3 and the suction tube 1 hold the scale 6 with a proper pressure without any damage to it since the spring 4 of shape memory alloy can be heated to a proper temperature by controlling the electric current to be applied to it and also because of desirable characteristics of shape memory alloy.

In practical operation, the instrument for inoculating bulb scales can be attached to, for example, a general-purpose 6-axis robot arm 7, as shown in FIG. 3. The robot arm 7 is operated to move the instrument 5 to a position above a scale to be picked up. The instrument 5 is operated to pick up a scale 6 according to the procedure explained with reference to FIGS. 2(A), 2(B), and 2(C). Then, the robot arm 7 is operated to move the instrument 5 to a position above an agar medium 8. The robot arm 7 is operated to move the instrument 5 downward to inoculate the scale 6 into the agar medium 8. The application of an electric current to the spring 4 of shape memory alloy is suspended and simultaneously the application of suction to the suction tube 1 is also suspended, so that the two fingers 2 and 3 part from the scale 6. Finally, the robot arm 7 is moved upward to complete one cycle of the steps for inoculation.

The instrument of the present invention may be applied to not only bulb scales but also delicate objects such as animals, plants, and foods for their mechanical handling.

What is claimed is:

1. An instrument for inoculating bulb scales which comprises an instrument body, a scale sucking finger having a suction means therein for attracting a scale, the sucking finger being rotatably joined to the instrument body, and a scale gripping finger, with one end thereof rotatably joined to the instrument body and with an intermediate part thereof connected to the instrument body with a spring made of shape memory alloy, the fingers being configured for gripping a scale between the suction means and a free end of the gripping finger.

2. An instrument for inoculating bulb scales as claimed in claim 1, wherein the suction means is a suction tube which passes through the scale sucking finger and leads to a suction pump.

* * * * *